United States Patent
Liversidge

(10) Patent No.: US 10,195,362 B2
(45) Date of Patent: *Feb. 5, 2019

(54) SAFETY NEEDLE DEVICE

(75) Inventor: Barry Peter Liversidge, Colchester (GB)

(73) Assignee: TIP-TOP.COM LTD (GB)

(*) Notice: Subject to any disclaimer, the term of this patent is extended or adjusted under 35 U.S.C. 154(b) by 0 days.

This patent is subject to a terminal disclaimer.

(21) Appl. No.: 13/640,090

(22) PCT Filed: Apr. 21, 2011

(86) PCT No.: PCT/GB2011/050806
§ 371 (c)(1),
(2), (4) Date: Oct. 9, 2012

(87) PCT Pub. No.: WO2011/131996
PCT Pub. Date: Oct. 27, 2011

(65) Prior Publication Data
US 2013/0030365 A1   Jan. 31, 2013

(30) Foreign Application Priority Data
Apr. 23, 2010  (GB) .................. 1006789.0

(51) Int. Cl.
*A61M 5/32* (2006.01)
*A61M 5/50* (2006.01)
*A61M 5/31* (2006.01)

(52) U.S. Cl.
CPC ......... *A61M 5/3202* (2013.01); *A61M 5/3204* (2013.01); *A61M 5/5086* (2013.01);
(Continued)

(58) Field of Classification Search
CPC .. A61M 5/3202; A61M 5/3204; A61M 5/326; A61M 2005/3109;
(Continued)

(56) References Cited

U.S. PATENT DOCUMENTS 5,616,135 A   4/1997 Thorne et al.
5,624,402 A *  4/1997 Imbert ................ A61M 5/3134
                                                 604/111

(Continued)

FOREIGN PATENT DOCUMENTS

WO     9748430     12/1997
WO     2009040601   4/2009
(Continued)

OTHER PUBLICATIONS

International Search Report, PCT International Application No. PCT/GB2011/050806, dated Oct. 5, 2011.

*Primary Examiner* — Kevin C Sirmons
*Assistant Examiner* — Leah Swanson
(74) *Attorney, Agent, or Firm* — Grossman Tucker Perreault & Pfleger PLLC

(57) ABSTRACT

A safety needle device for a medical injector supporting a needle projecting forwardly from the front of the injector body has a tubular sleeve for a supported needle, the sleeve being slidable rearwardly with respect to the needle to expose at least the tip thereof. The sleeve has a forward end for contacting an injection site and a removable cover is engaged in sealing contact with the forward end of the sleeve. The sleeve may have an in-turned flange at its forward end defining an orifice through which the needle projects when the sleeve slides rearwardly. The removable cover may effect a seal to that flange.

18 Claims, 9 Drawing Sheets

(52) U.S. Cl.
CPC ............... *A61M 2005/312* (2013.01); *A61M 2005/3109* (2013.01)

(58) Field of Classification Search
CPC .... A61M 2005/312; A61M 2005/3268; A61M 5/5086; A61M 2005/319; A61M 2005/311; A61M 2005/3107; A61M 2005/3117; A61M 2005/3118
USPC ... 604/164.08, 192, 193, 197, 198, 263, 111
See application file for complete search history.

(56) References Cited

U.S. PATENT DOCUMENTS

| | | | |
|---|---|---|---|
| 5,647,849 A | 7/1997 | Kalin | |
| 5,749,860 A | 5/1998 | Kyte | |
| 5,820,605 A * | 10/1998 | Zdeb | A61M 5/3202 604/110 |
| 2002/0193737 A1* | 12/2002 | Popovsky | A61M 5/326 604/110 |
| 2005/0015055 A1 | 1/2005 | Yang | |
| 2005/0075611 A1* | 4/2005 | Hetzler | A61L 2/0011 604/192 |
| 2005/0277892 A1* | 12/2005 | Chen | A61M 5/3202 604/192 |
| 2011/0301548 A1* | 12/2011 | Young | 604/200 |
| 2011/0319864 A1* | 12/2011 | Beller et al. | 604/506 |

FOREIGN PATENT DOCUMENTS

| | | |
|---|---|---|
| WO | 2009081133 | 7/2009 |
| WO | 2009155277 | 12/2009 |
| WO | 2010094916 | 8/2010 |

* cited by examiner

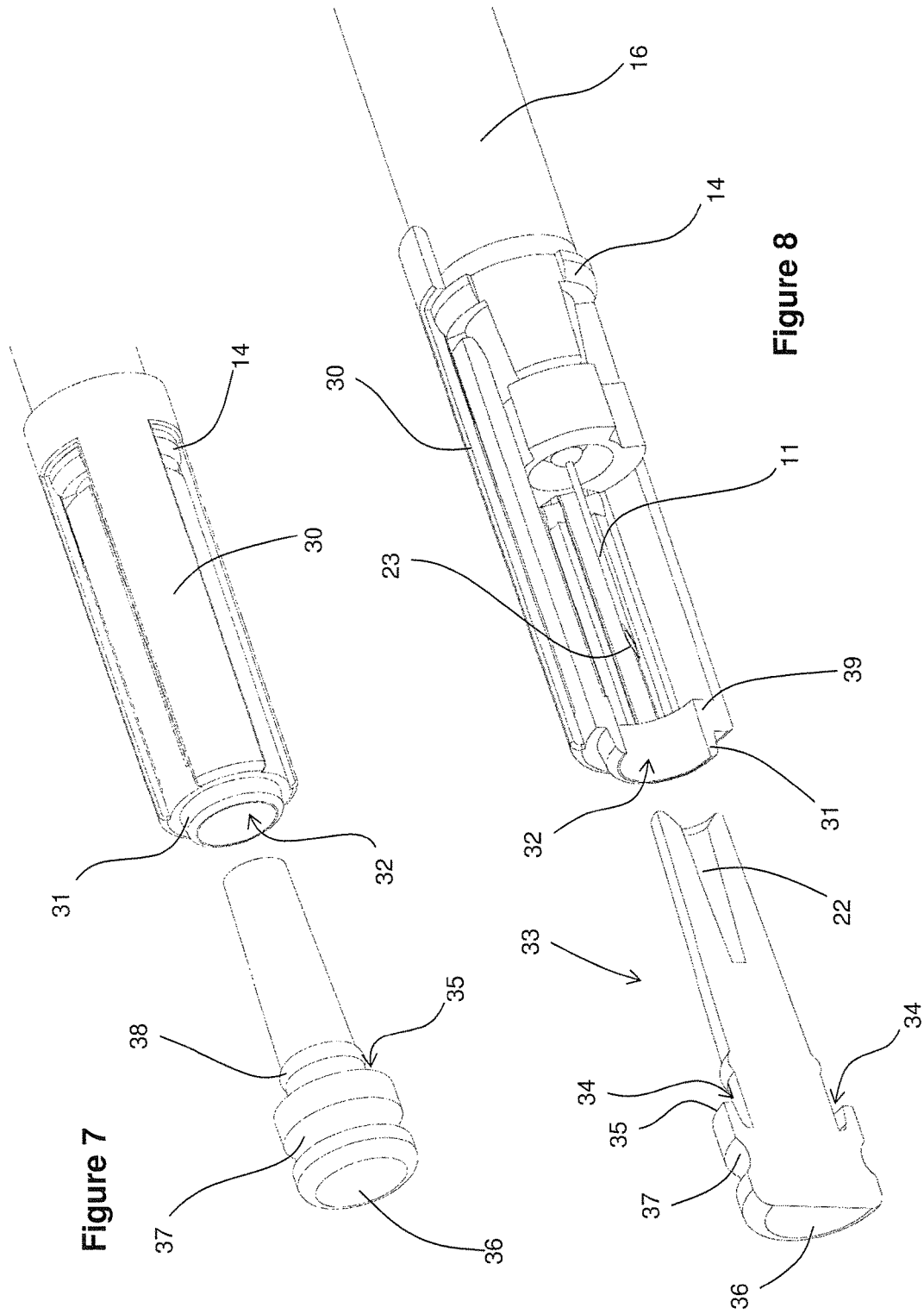

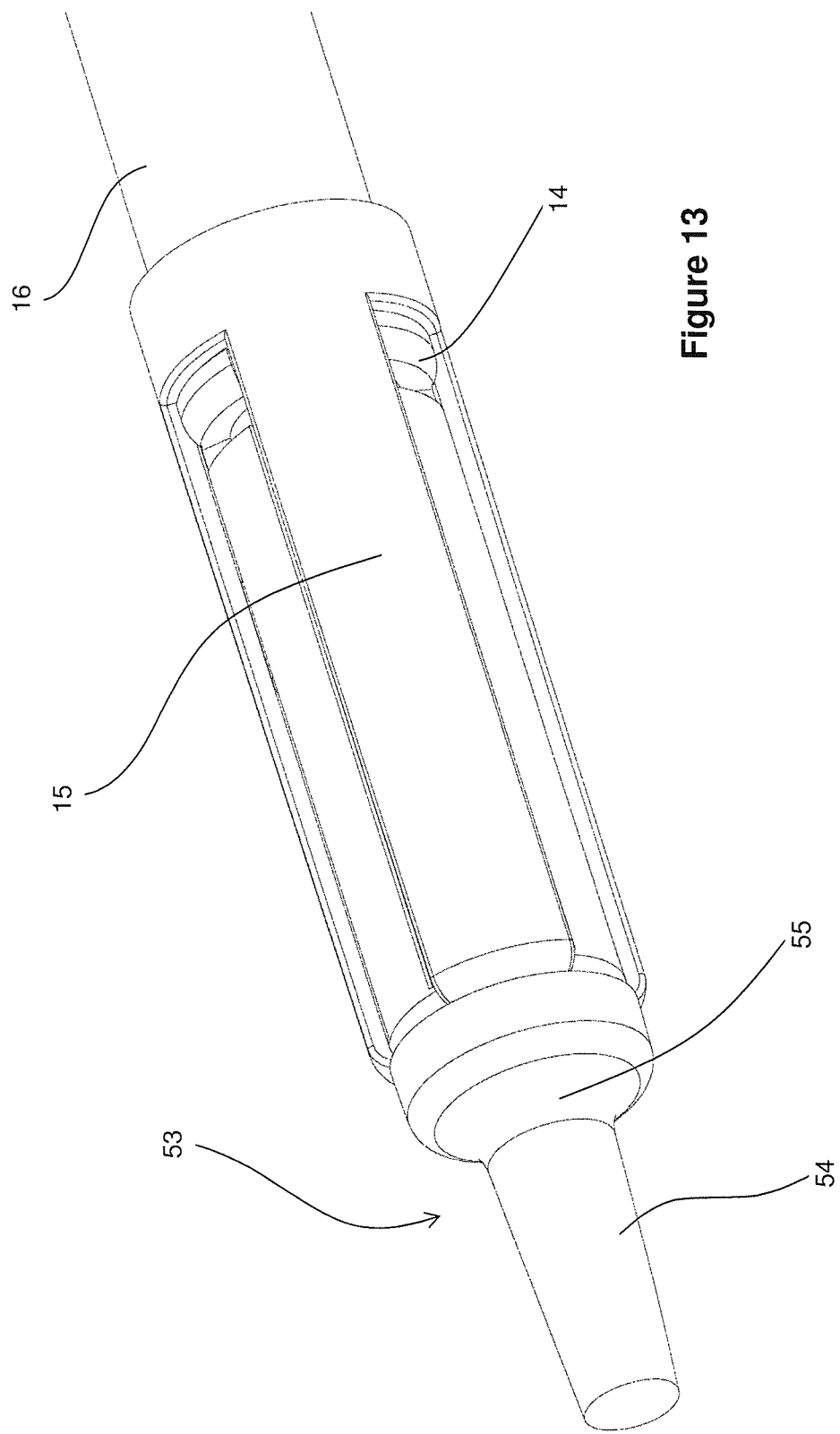

SAFETY NEEDLE DEVICE

CROSS REFERENCE TO RELATED APPLICATION

The present application is the U.S. national stage application of International Application PCT/GB2011/050806, filed Apr. 21, 2011, which international application was published on Oct. 27, 2011 as International Publication WO 2011/131996. The International Application claims priority of British Patent Application 1006789.0, filed Apr. 23, 2010.

This invention relates to a safety needle device for a medical injector either directly or indirectly supporting a needle.

The safety device of this invention is intended for use with a medical needle used to penetrate a human or animal body, or for other medical uses such as the penetration of a pierceable membrane of an intravenous medication system. In the following all medical uses of the needle safety device will be described simply as the penetration of a body, even though specific embodiments may be intended for other medical uses.

Throughout this specification the terms "forward" and "forwardly" used in relation to the needle safety device and a syringe for use therewith refer to those ends of the components which are approached to a body when a procedure is to be performed, and the direction towards those ends. Conversely, the terms "rearward" and "rearwardly" refer to those ends of the components opposed to the forward ends and the direction away from those forward ends.

Safety needle devices are being increasingly used with medical injectors, to confer either passive or active safety on the needle. Such a device frequently has a sleeve which is slidable with respect to the injector or syringe, such that the needle is exposed by rearward sliding movement of the sleeve with respect to the injector or syringe and subsequent to the performance of an injection, the sleeve slides forwardly once more again to confer protection to the needle. With many such devices, the sleeve is locked in its forward position following the performance of an injection, so that the needle cannot be re-used.

It is the conventional practice with a safety needle device as described above to provide a cover for the needle and which engages the needle hub or part of the syringe which mounts the needle. Such a cover is applied in a sterile environment during the manufacture of the device so that sterility of the needle itself is assured, up to the point at which the cover is pulled away to expose the needle ready for use. In the case of a pre-filled syringe having a needle permanently fitted thereto, the cover will also serve as a stopper for the needle, to prevent leakage of the drug out of the sharp tip of the needle. Such a cover is of a soft resilient rubber or similar elastomeric material to allow the creation of a seal at the rearward end of the cover against the needle hub or the injector or syringe and also to allow the needle tip to penetrate the material of the cover without damaging the needle tip.

Though such a cover may maintain adequate sterility for the needle itself until the device is to be used, the free end of the sleeve is not protected prior to the performance of an injection. It could happen that the free end of the sleeve, which is pressed against the injection site at the time of performing an injection, is contaminated in some way, either during storage or even immediately before use. If a contaminated free end of the sleeve is allowed to move laterally over the skin at the injection site, the penetration of the needle into that site may carry with it some contaminant, leaving a patient open to infection.

It is a principal aim of the present invention to provide a safety needle device which minimises the likelihood of the forward end of the sleeve becoming contaminated prior to use of the device to perform an injection.

According to this invention, there is provided a safety needle device for a medical injector supporting a needle projecting forwardly from the front of the injector body, which device comprises a tubular sleeve for a supported needle and slidable rearwardly with respect thereto to expose at least the tip of the supported needle, the sleeve having a forward end for contacting an injection site, and said forward end of the sleeve having a removable cover engaged in sealing contact therewith.

The tubular sleeve confers protection on the needle, both before and after use of the injector, to minimise the likelihood of a needle-stick injury and also to prevent damage to the tip of the needle before use. With this invention, it will be appreciated that the part of the sleeve which contacts the injection site of a patient is protected by the removable cover which maintains a sealing contact with that part of the sleeve until the cover is removed from the sleeve.

It may be sufficient for the removable cover to effect a seal to the forward end of the sleeve, though in preferred embodiments where the removable cover is fitted to the sleeve under sterile conditions, a substantially sterile seal may be created at the forward end of the sleeve.

As with the known safety needle devices, it is preferred that the removable cover is formed from a resiliently deformable material such as a natural or synthetic rubber. The forward end of the sleeve may define an orifice through which the needle projects when the sleeve slides rearwardly with respect to the injector and in this case, the removable cover preferably is located in the orifice so as to effect a seal to the sleeve in the region of the orifice.

A typical safety needle device has a sleeve with an in-turned flange at its forward end and which defines the orifice. The outer face of that flange contacts the injection site and for such a sleeve, the removable cover should be profiled to effect a seal to the outer face of that flange. Preferably, the removable cover has an annular groove in which is received the flange and the width of the groove may be slightly less than the axial width of the flange such that the side faces of the groove are maintained in sealing contact with the flange, by the tensile force generated in the part of the cover between the two side faces of the groove. This tensile force may assist in maintaining the sterility of the outer face of the flange which contacts the injection site, when the device is used to perform an injection.

In an alternative embodiment, the sleeve may have a forwardly-projecting lip at its forward end, with the foremost part of that lip contacting the injection site during the performance of an injection. In this case, the removable cover should be profiled in a complementary manner to the lip, such that a seal is effected thereto.

The removable cover may project forwardly from the forward end of the sleeve and advantageously is profiled to facilitate the manual gripping of that part of the removable cover, to allow the cover to be pulled away from the sleeve immediately before use of the device.

As with the known forms of safety needle device, the removable cover may extend rearwardly within the sleeve and effect a seal to the injector, nose of a syringe or needle hub, depending upon the application. In addition, the removable cover may have an axial recess extending thereinto from the rearward end of the cover and into which the needle is received. The depth of the recess preferably is less than the projecting length of the needle, such that the tip of the needle penetrates the material of the removable cover, so as to be sealed thereby. In addition, the cover then may serve as a stopper for the needle, to prevent dribbling of liquid drug from the tip of the needle in the case of a pre-filled syringe having a needle fitted thereto.

The length of the removable cover within the sleeve may be slightly greater than the distance between the part of the injector engaged by the rearward end of the cover and the forward end of the sleeve, such that when installed, the part of the cover within the sleeve is axially compressed slightly, thereby maintaining a seal between the rear end of the cover and the injector, syringe or needle hub.

A sealant gel or similar substance may be provided between the forward end of the sleeve and that part of the cover which is engaged therewith, in order to ensure the effectiveness of the seal following the manufacture of the safety needle device. An alternative is to provide a low-tack adhesive connection between the forward end of the sleeve and that part of the cover which is engaged therewith, the adhesive seal being broken by pulling away the cover, from the device. Another possibility is to provide a tamper-evident seal around the junction between the sleeve and the cover and which seal must be broken or peeled away prior to use.

By way of example only, certain specific embodiments of safety needle device of this invention will now be described in detail, reference being made to the accompanying drawings in which:

FIG. 7 shows the removable cover of the second embodiment, pulled away from the sleeve;

Figure 9:
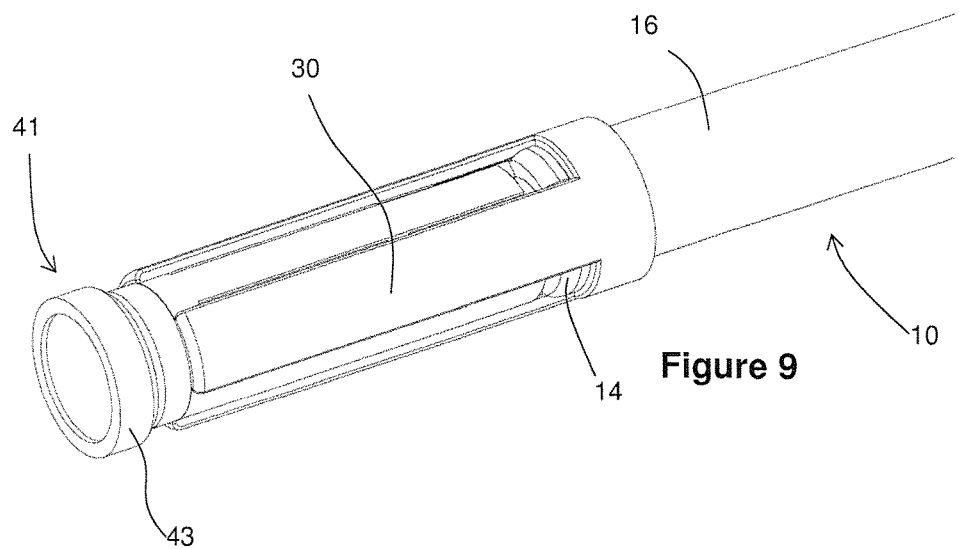
Figure 10:
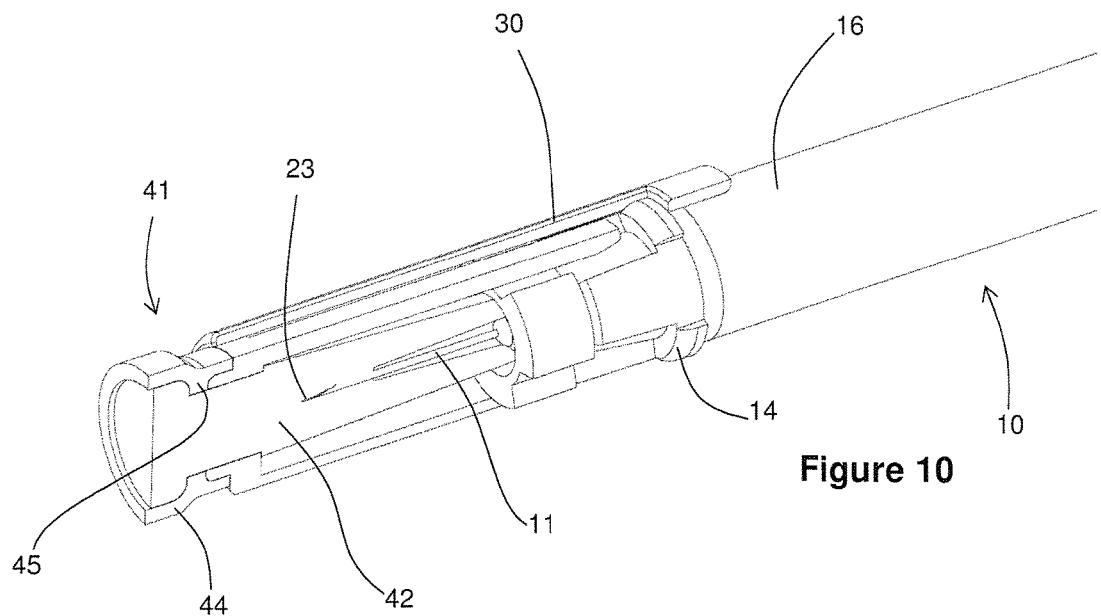
Figure 11:
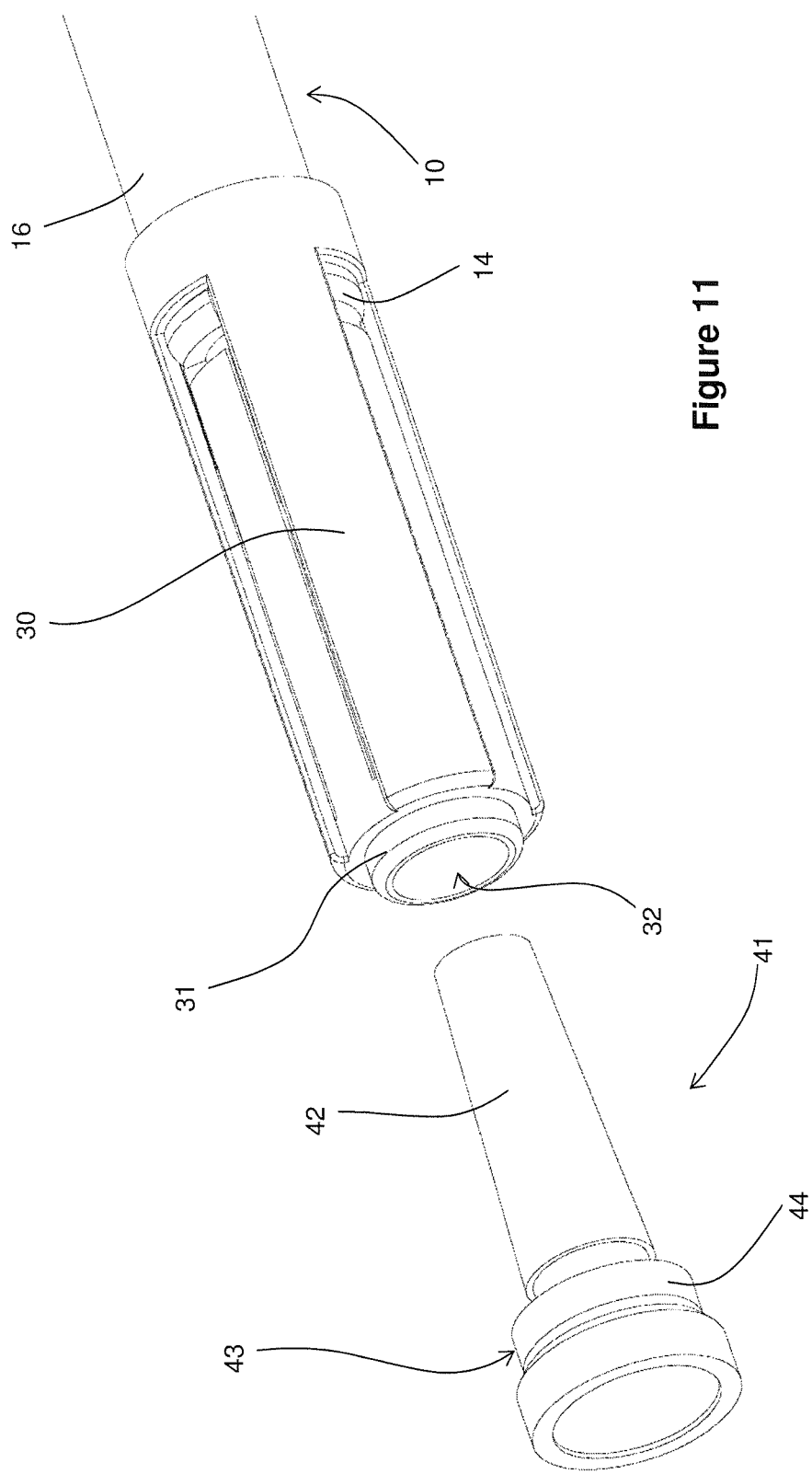
Figure 12:
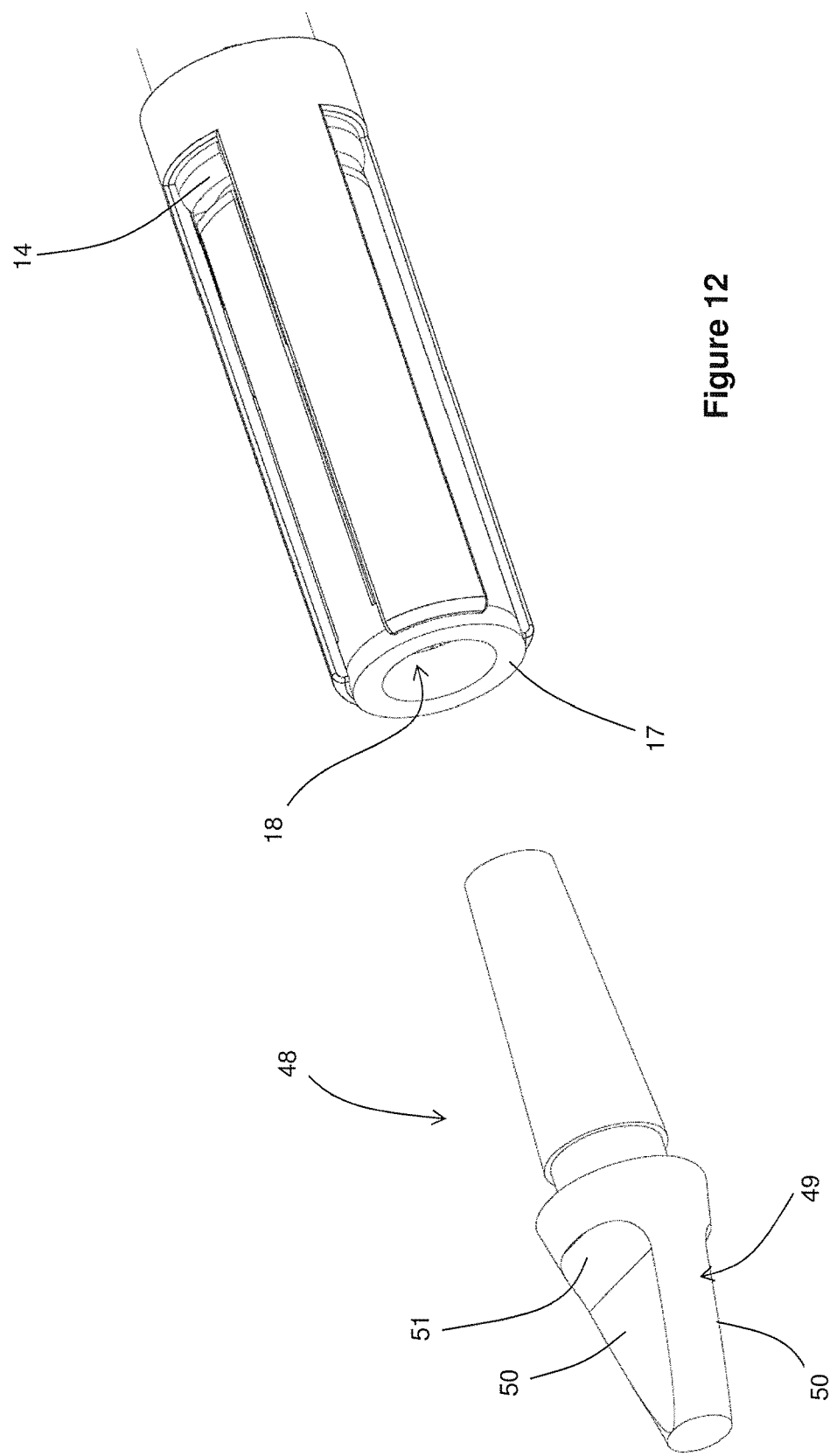

FIG. 8 corresponds to FIG. 7 but shows in section both the safety needle device and the removable cover;

FIGS. 9 and 10 are isometric views of a third embodiment, with FIG. 10 partly in section;

FIG. 11 shows the third embodiment of FIG. 9, but with the removable cover pulled away from the sleeve;

FIG. 12 shows a fourth embodiment generally corresponding to the first embodiment but having a different external profile to the removable cover; and FIG. 13 shows yet another embodiment of removable cover.

FIGS. 1 to 4 show the first embodiment of safety needle device of this invention, intended for use with a medical syringe 10 having a staked-in needle 11. The safety needle device 12 fits on to a nose 13 provided at the forward end of the syringe, rearwardly of the needle, and includes a mount 14 and a protective sleeve 15 which normally covers the needle but which is arranged for rearward sliding movement over the barrel 16 of the syringe, so as to expose the needle.

The sleeve 15 has at its forward end an in-turned flange 17 which defines an orifice 18 through which the needle 11 projects, when the sleeve has slid rearwardly with respect to the syringe. In performing an injection, the flange 17 is engaged with an injection site and the syringe is pushed forwardly with respect to the sleeve, so projecting the needle 11 through the orifice 18 and into the body mass at the injection site. After completion of the injection, the syringe is pulled away from the injection site while the sleeve remains stationary engaged with that site, until the sleeve is in its fully forward, protecting position whereat the sleeve is locked to prevent rearward movement for a second time.

The precise configuration of the safety needle device, insofar as it concerns a sleeve arranged for rearward sliding movement, the mounting of that sleeve on a syringe, and the locking of the sleeve in its protecting position following the performance of an injection, all form no part of this invention and so will not be described in greater detail here, though these features are well known and understood by those skilled in this art.

With this embodiment, there is provided a removable needle cover 20 of an elastomeric material. The cover 20, at its rearward end 21, engages the nose 13 of the syringe 10 to effect a seal thereagainst. The cover has an axial recess 22 extending into the cover from its rearward for receiving the needle 11, the sharp tip 23 of the needle penetrating the material of the cover so as both to effect a seal thereagainst and also to serve as a stopper, to prevent liquid drug in the syringe from dribbling out of the needle, before use. The needle cover has an annular groove 24 into which the flange 17 is received, the groove 24 being configured to be in sealing contact with the outer face 25 of the flange. The engagement of the flange 17 in the groove also serves to resist inadvertent rearward movement of the sleeve 15, until the removable cover is pulled away from the sleeve.

The length of the cover, between the rearward face 26 of the groove and the rearward end of the cover, is slightly longer than the distance between the nose of the syringe and the inner face of the flange 17 so that the region of the cover between its rearward end and the face 26 of the groove 24 is slightly in compression, thereby maintaining a seal against the nose of the syringe. In addition, the width of the groove 24, between its rearward face 26 and the forward face thereof contacting the outer face 25 of flange 17, is slightly less than the width of the flange 17, in the axial direction. The reception of the flange 17 in the groove thus slightly stretches and so generates a tensile force in the material of the cover in the region of the groove, so that the forward face of the groove is urged into engagement with the outer face 25 of the flange, to assist the maintenance of a seal therebetween. The device will normally be manufactured under sterile conditions and if the tensile force is sufficiently high, the seal to the outer face of the flange may be maintained sterile until the cover is removed, prior to use of the device.

Figure 1:
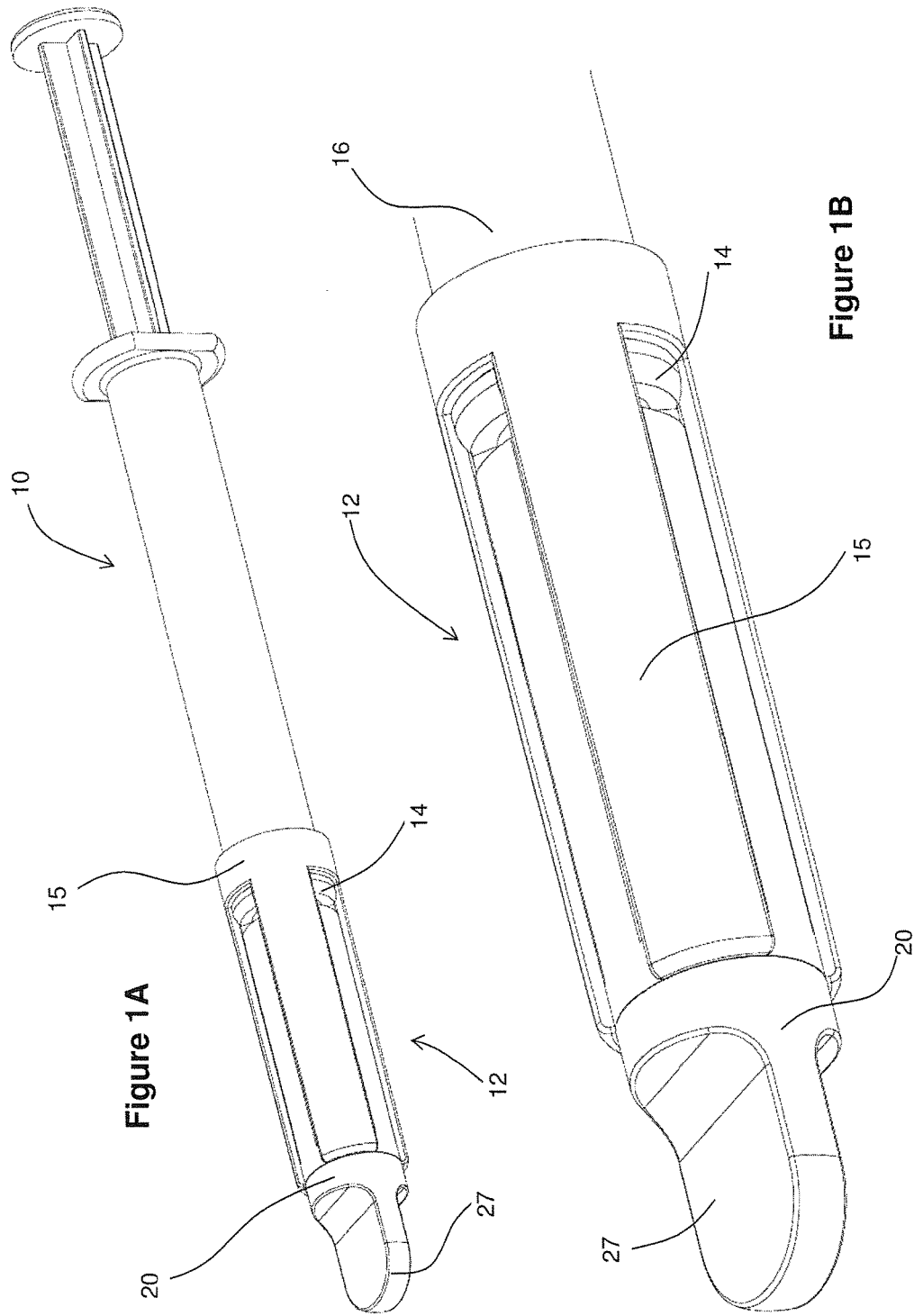
FIG. 1A is an isometric view of a syringe fitted with a first embodiment of safety needle device and FIG. 1B is a view on an enlarged scale of the safety needle device as shown in FIG. 1A.
Figure 2:
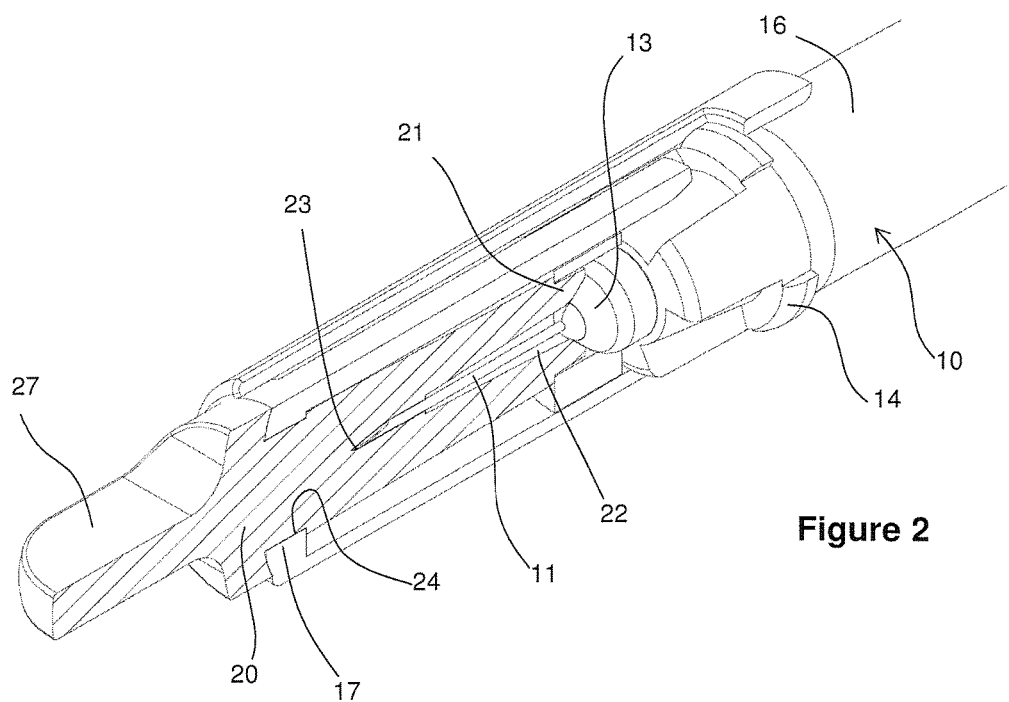
FIG. 2 is an isometric part-sectional view of the first embodiment shown in FIG. 1B.
Figure 3:
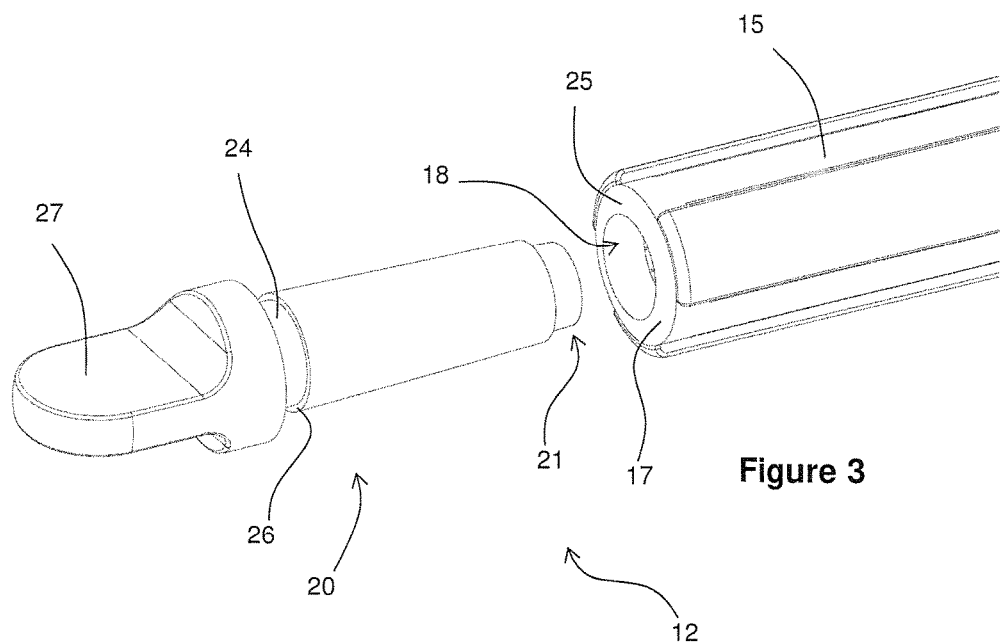
FIG. 3 is an isometric view of the device of FIG. 1B but with the removable cover pulled away from the sleeve.
Figure 4:
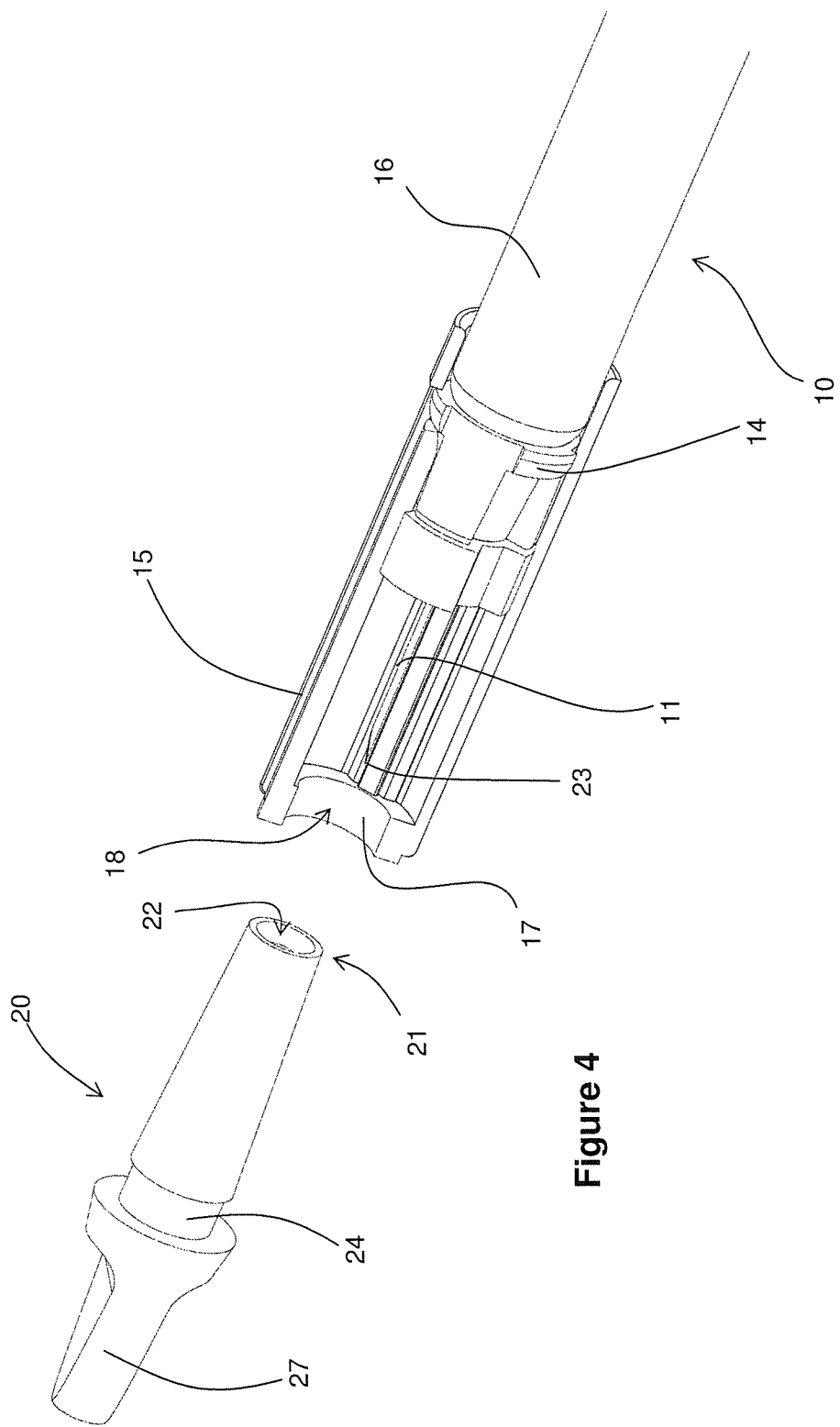
FIG. 4 shows partly in section the device of FIG. 3, with the cover pulled away.
Figure 5:
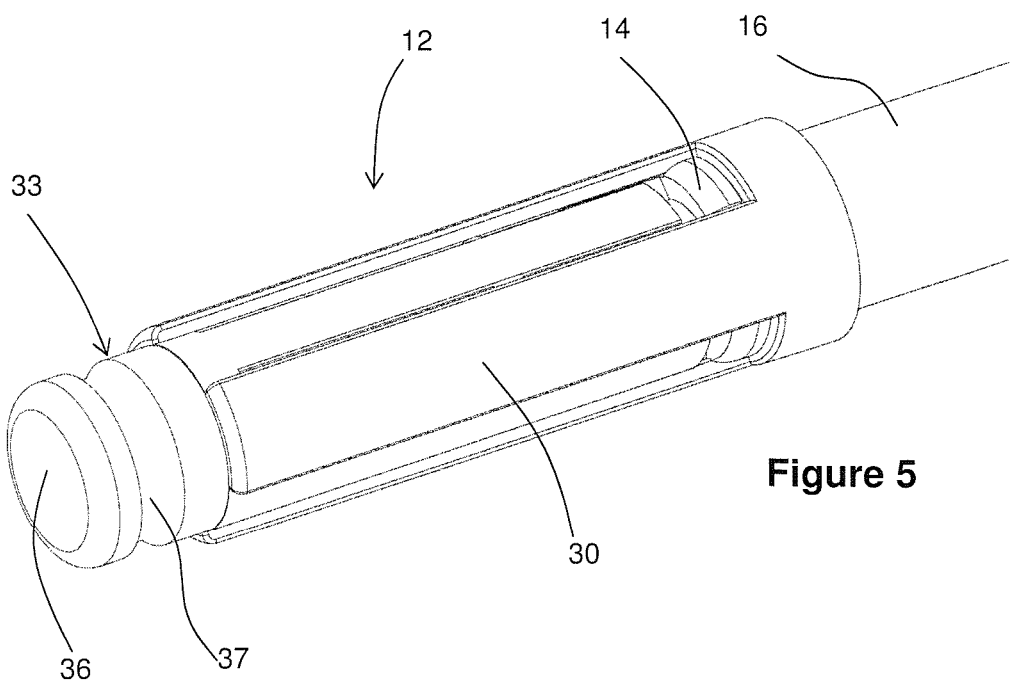
FIG. 5 is an isometric view of a second embodiment of safety needle device.
Figure 6:
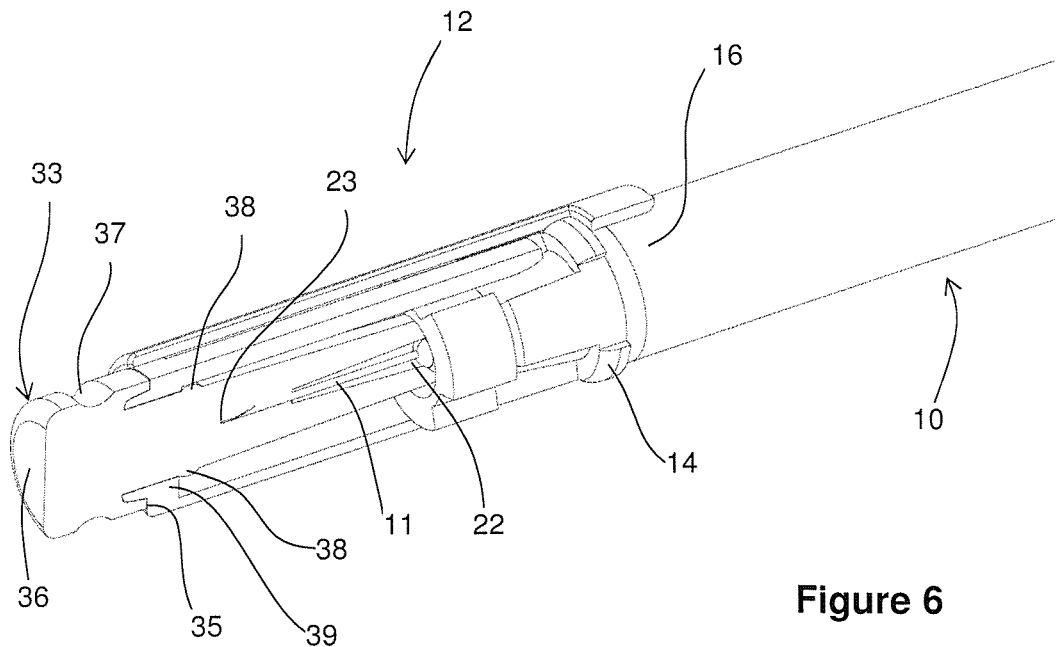
FIG. 6 is a view similar to FIG. 5, but partly in section.

Forwardly of the groove 24, the cover is shaped to provide a tab 27 which may readily be gripped between the thumb and a finger of a user, to allow the cover to be pulled away from the syringe, as shown in FIGS. 3 and 4. This exposes the forward outer face 25 of the flange 17 and also allows the sleeve 15 to move rearwardly. In view of the resilient nature of the material of the cover, pulling on the tab 27 will allow the flange 17 to ride out of the groove 24 of the cover and so be sufficient to pull the cover away from the safety needle device.

FIGS. 5 to 8 show a second embodiment of safety needle device having a different profile at the forward end of the sleeve and a cover of a complementary form to that profile of the sleeve. In other respects, the arrangement of the safety needle device of this second embodiment corresponds to that of the first embodiment and will not be described again here.

In this second embodiment, the forward end of the sleeve 30 has an axially-projecting lip 31 with the bore 32 of that lip being contiguous with the bore of the sleeve at the forward end thereof. The cover 33 has an axial recess 34 which closely receives the lip 31 and also an end face 35 which engages the annular face at the forward end of the sleeve, around the lip 31. Forwardly of the recess 34, the cover 33 is again configured for manual gripping in order to allow the cover to be pulled away from the sleeve 30, in this case the cover having a head 36 with an annular groove 37 defined between that head 36 and the main part of the cover.

Within the sleeve 30, the cover has an annular rib 38 which engages behind the flange 39 at the forward end of the sleeve. This serves both to prevent accidental rearward movement of the sleeve until the cover has been removed and also to ensure the rearward end of the sleeve effects a seal to the nose of the syringe—as with the previous embodiment, the length of the cover between the rib 38 and the rearward end is slightly greater than the distance between the inner face of the flange and the nose of the syringe, so maintaining that part of the cover in compression.

Also as with the previous embodiment, there is an axial recess 22 in the cover and into which the needle is received, with the tip of the needle penetrating the material of the cover so as to effect a seal to the needle tip and also to stopper the end of the needle.

With the second embodiment, the removable cover 33 is formed in one piece, from a resilient elastomeric material. The third embodiment shown in FIGS. 9 to 11 is similar to the second embodiment except that the removable cover 41 is formed in two pieces: the main piece 42 is of an elastomeric material (as with the previous embodiment) and serves to effect a seal against the tip of the needle as well as the nose of the syringe; and a secondary piece 43 mounted on the main piece externally of the sleeve 30 and in the form of a relatively rigid ring 44. The head of the main piece 42 is received within the ring 44 and is retained therein by an annular protrusion 45 which also defines the internal profile at the rearward end of the ring, for receiving the lip 31 of the sleeve. The seal to the forward end of the sleeve is thus achieved against the ring 44 as well as internally within the bore 32 at the forward end of the sleeve.

Having regard to the relatively rigid ring 44, distortion of the forward end of the removable cover is minimised when the forward end is gripped to pull the cover away from the sleeve, and so the likelihood of accidental contact with the forward end of the sleeve on removing the cover is correspondingly reduced.

The fourth embodiment is shown in FIG. 12 and broadly corresponds to that of FIGS. 1 to 4 and similar parts are given like reference characters and will not be described again here. The fourth embodiment differs from the first in that the configuration of the part of the removable cover 48 externally of the sleeve is adapted to minimise the likelihood of accidental contact with the forward end of the flange, on pulling the removable cover away from the remainder of the safe needle device, to prepare that device ready for use. To this end, the external part 49 of the cover is of a generally conical form but with two diametrically-opposed parallel flats 50 formed therein, and ramp surfaces 51 leading from those flats back to the conical surface adjacent the groove 24.

The configuration of the external part 49 of the removable cover is such that a user's fingers are maintained clear of the forward end of the sleeve 30 when that external part is gripped for pulling away from the sleeve. In this way, the likelihood of accidental contact with the forward end of the sleeve is minimised.

The removable cover 53 shown in FIG. 13 is similar to the cover 48 of the fourth embodiment but the external profile of the part 54 of the cover projecting from the forward end of the sleeve 15 is of a simple conical form, of a relatively small diameter. This part 54 is easy to grip between the fingers but it is difficult to impart a rotational movement to the cover 53 so minimising the likelihood of damage to the sharp tip of the needle within the device. Moreover, by having a relatively small diameter for the projecting part 54 of the cover, the part 55 of the cover immediately rearwardly thereof serves as a shield assisting the protection of the forward end of the sleeve 15 and reduces the likelihood of contact of that forward end by the fingers of a user.

With all of the above embodiments, the seal between the forward end of the sleeve and the removable cover may be enhanced by providing a non-setting sealant gel or similar composition on the mating faces of the cover and the forward end of the sleeve. In the alternative, an adhesive may be provided between those faces and which must be released, in order to allow the cover to be pulled away. For this purpose, a low-tack adhesive may be employed such that axial pulling on the exposed external part of the cover is sufficient to release the adhesive. When a gel, adhesive or similar agent is provided to enhance the seal, if the cover is assembled to the sleeve under sterile conditions, the forward end of the sleeve may also be maintained sterile until the cover is pulled away from the sleeve, to prepare the device for use.

Another possibility would be to provide a frangible seal around the junction between the removable cover and the forward end of the sleeve. For example, that seal may be in the form of a self-adhesive paper or plastic material strip wrapped around the junction and which must be torn away or otherwise broken, to allow the removable cover to be pulled away from the sleeve. Such a seal strip may maintain the sterility of the forward end of the sleeve but may also serve as a tamper-evident seal.

The invention claimed is:

1. A safety needle device for a medical injector having a barrel, said barrel having a front end for supporting a needle having a sharp tip such that the needle projects forwardly from said front end, wherein said device comprises:
   a tubular sleeve for covering the needle, said sleeve being slidable rearwardly with respect to the needle to expose at least the tip of the needle, the sleeve having a forward end comprising a forward facing surface for contacting an injection site, wherein:
      the sleeve comprises an in-turned flange at the forward end;
      the in-turned flange defines an orifice through which the needle projects when the sleeve is slid rearwardly; and
      the in-turned flange further comprises a rearward facing surface;
   a removable cover comprising a resiliently deformable material, wherein:
      the cover extends through the orifice at the forward end of the sleeve;
      the cover further comprises a part which projects rearwardly into the sleeve and which receives and sealingly engages with the sharp tip of the needle;
      the cover further comprises a rearward facing surface in sealing contact with the forward facing surface of the sleeve; and the cover further comprises a forward facing surface in contact with the rearward facing surface of the flange.

2. The safety needle device as claimed in claim 1, wherein the removable cover comprises an annular groove, and the in-turned flange is received within the annular groove.

3. The safety needle device as claimed in claim 2, wherein:
the annular groove comprises confronting side faces with an axial width therebetween;
the in-turned flange has an axial width;
an axial width of the annular groove between said confronting side faces is less than the axial width of the in-turned flange whereby the resiliently deformable material of the removable cover in the region of the annular groove is stretched on receiving the flange in the groove, so generating a tensile force in said material to maintain contact between the removable cover and the forward end of the sleeve; and
a first one of the confronting side faces provides the rearward facing surface of the cover and a second one of the confronting side faces provides the forward facing surface of the cover.

4. The safety needle device as claimed in claim 1, wherein the sleeve has a forwardly-projecting lip at its forward end, the forwardly-projecting lip comprising the forward facing surface for contacting an injection site, and the removable cover is profiled to effect a seal to said lip.

5. The safety needle device as claimed in claim 4, wherein the removable cover has one of an annular groove or an annular recess in which said lip is received.

6. The safety needle device as claimed in claim 1, wherein a part of the removable cover projects forwardly from the forward end of the sleeve, said part having a profile configured to facilitate manual gripping of the removable cover and the pulling thereof away from the sleeve before use of the device.

7. The safety needle device as claimed in claim 1, wherein a rearward end of the removable cover is profiled for effecting sealing engagement with at least one of a needle hub supporting the needle and a part of an injector at the forward end thereof.

8. The needle safety device as claimed in claim 7, wherein a length of the cover between the forward facing surface and the rearward end is longer than a distance between the rearward facing surface of the flange and the needle hub supporting the needle or the part of an injector at the forward end thereof.

9. The safety needle device as claimed in claim 1, wherein said part of the removable cover that projects rearwardly into the sleeve has an axial recess for receiving a part of a supported needle.

10. The safety needle device as claimed in claim 9, wherein a depth of the axial recess is less than a projecting length of the needle, such that fitting of the device to the needle causes the sharp tip of the needle to penetrate said resiliently deformable material to be sealed thereby.

11. The safety needle device as claimed in claim 1, wherein a sealing agent is provided to effect a seal between the forward end of the sleeve and a part of the removable cover in engagement with said forward end.

12. The safety needle device as claimed in claim 11, wherein the sealing agent is one of a sealing gel or an adhesive composition.

13. The safety needle device as claimed in claim 11, wherein there is a junction between the forward end of the sleeve and the removable cover, a peripheral region being defined around said junction, and the sealing agent comprises a tamper-evident seal adhered around said peripheral region of the junction between the forward end of the sleeve and the removable cover.

14. The safety needle device as claimed in claim 1, wherein the removable cover has a radially outwardly facing annular groove in which the in-turned flange is received.

15. The needle safety device as claimed in claim 14, wherein the annular groove is formed in an outer surface of the removable cover.

16. The safety needle device as claimed in claim 1, wherein the sleeve has a forwardly-projecting lip at its forward end, said lip having a bore that is contiguous with a bore of said sleeve rearward of said lip, wherein said forwardly-projecting lip comprises the forward facing surface for contacting an injection site, and the removable cover is profiled to effect a seal to said lip.

17. The needle safety device as claimed in claim 1, wherein the removable cover includes an annular rib, and the forward facing surface of the cover is provided by the rib.

18. A safety needle assembly, comprising:
a medical injector comprising a barrel comprising a front end, the medical injector further comprising a needle supported in the front end of the barrel, the needle having a sharp tip; and
a safety needle device, the safety needle device comprising an outer tubular sleeve and a cover,
wherein the outer tubular sleeve:
is coupled to the medical injector so as to cover the needle when the outer tubular sleeve is in a first position;
comprises a forward end comprising a forward facing surface for contacting an injection site, the sleeve comprising an in-turned flange at the forward end, the in-turned flange defining an orifice; and
is coupled to the barrel such that the it is slidable rearwardly with respect to the needle to a second position in which the sharp tip extends through the orifice such that at least a portion of the needle is exposed; and
wherein the cover:
is removably coupled to the outer tubular sleeve; and
is formed of a resiliently deformable material; and
when the cover is coupled to the outer tubular sleeve and the outer tubular sleeve is in the first position, the cover extends through the orifice at the forward end of the sleeve, and the cover comprises a part that projects rearwardly into the sleeve, wherein the part is configured to receive and sealingly engage with the sharp tip of the needle, and the cover further comprises a rearward facing surface in sealing contact with the forward facing surface of the sleeve and a forward facing surface in contact with a rearward facing surface of the flange.

* * * * *